United States Patent [19]

Adachi

[11] Patent Number: 4,684,673

[45] Date of Patent: Aug. 4, 1987

[54] SURGICAL CEMENT FROM AMORPHOUS TRICALCIUM PHOSPHATE, POLY(CARBOXYLIC ACID) AND WATER

[75] Inventor: Toshio Adachi, Osaka, Japan

[73] Assignee: Meishintoryo Co. Ltd., Osaka, Japan

[21] Appl. No.: 750,301

[22] Filed: Jul. 1, 1985

[30] Foreign Application Priority Data

Jul. 2, 1984 [JP] Japan ............................... 59-137000

[51] Int. Cl.⁴ .............................................. C08L 33/02
[52] U.S. Cl. .................................... 523/116; 523/113; 523/115; 524/417
[58] Field of Search ....................... 523/116, 113, 115; 524/417

[56] References Cited

U.S. PATENT DOCUMENTS

| | | | |
|---|---|---|---|
| 4,089,830 | 5/1978 | Tezuka et al. | 106/35 |
| 4,243,567 | 1/1981 | Potter | 524/417 |
| 4,542,167 | 9/1985 | Aoki | 523/109 |

*Primary Examiner*—Harold D. Anderson
*Attorney, Agent, or Firm*—Kerkam, Stowell, Kondracki & Clarke

[57] ABSTRACT

Here disclosed are surgical cements useful for filling defect parts and vacant part of bones and teeth, which comprises (a) self-hardening amorphous tricalcium phosphate powder, (b) a component (B) of a surgically acceptable water-soluble poly(carboxylic acid), and (c) water and which is prepared by mixing amorphous tricalcium phosphate powder, the component (B) and water or mixing amorphous tricalcium phosphate and an aqueous solution of the component (B), then kneading the mixture.

12 Claims, No Drawings

SURGICAL CEMENT FROM AMORPHOUS TRICALCIUM PHOSPHATE, POLY(CARBOXYLIC ACID) AND WATER

FIELD OF THE INVENTION

The present invention relates to a surgical cement, more particularly the invention petains to a surgical cement containing amorphous tricalcium phosphate as the principal component and a method for preparing the same.

DESCRIPTION OF THE PRIOR ART

To date, many materials applicable to living body such as plastic materials or various kinds of metals, for example, gold, silver, alloys of palladium, Ni-Cr alloys, Co-Cr alloys, amalgam, stainless steel, titanium alloys have been proposed and they have been used in many fields such as orthopedics and dentistry. These materials have many applications for tooth crown, root of tooth, and further they are tried to use in artificial bones, artificial joints or the like. They have a high reliability in their mechanical strength and are capable of precision processing, while they suffer various undesirable modification such as dissolution, corrosion, deterioration due to the severe environmental conditions in living body, and are fatigued during the long-term service and accompany a foreign substance forming reaction (for instance, the formation of secondary caries).

Then, ceramics materials having a relatively good affinity for living tissues are recently paid great attention.

For example, there are proposed such as artificial bones, artificial joints and artificial root of the tooth composed of $Al_2O_3$ single crystal or sintered body thereof or those constituted by hydroxyapatite.

However, these inplant materials have disadvantages such that they are too hard and fragile, these being common to the ceramics. Many problems to be solved still remain in order to adopt them as the material for artificial bones and root of the tooth.

On the other hand, a cement in which orthophosphoric acid solution is conventionally used as the setting solution, in the field of surgical cement. As such cement, there are known, for instance, zinc phosphate cement obtained by kneading zinc oxide with about 70% aqueous orthophosphoric acid solution and silicate cement which is used in the form of a product kneaded silicate glass with aqueous phosphoric acid solution and the like. However, these cements are highly acidic due to the phosphoric acid used and accordingly, they have pulpal injury effect and moreover they are insufficient in the adhesion with teeth.

On the contrary, U.S. Pat. Nos. 3,655,605, 3,741,926, 3,751,391 and 3,804,794 propose zinc oxide-polycarboxylate cement in which aqueous poly(carboxylic acid) solution having a weak pulpal injury is used instead of the aqueous orthophosphoric acid solution.

In addition, ionomer cements are developed in order to modify the compressive strength of cements and in said ionomer cements, fluoroaluminosilicate is used in place of zinc oxide, which is set with an aqueous solution of poly(carboxylic acid) (see, for instance, U.S. Pat. Nos. 3,814,717 4,016,124, 4,089,830 and British Patent No. 1,316,129). However, the ingredients used in these cements chemically differ from those of the teeth and bones and therefore, many problems to be overcome still remain, such that these are less compatible to living tissues, that they irritate pulpal tissues and that they penetrate into dentinal tubule and the like.

Moreover, in order to adjust the setting speed of carboxylate cements composed of zinc oxide and poly(carboxylic acid), there are proposed such as a composition which is prepared from the carboxylate cement by adding, as a filler, a small amount of calcium phosphate powder thereto (see, U.S. Pat. Nos. 3,655,605, 3,751,391 and 4,288,355) and a cement composition obtained by mixing hydroxyapatite as principal component with an inorganic powder such as ZnO, CaO, $Al_2O_3$, $Ca_3(PO_4)_2$, $SiO_2$ and poly(carboxylic acid) (see, for example, Japanese Patent Laid-Open Appln. No. 83605/1983).

Furthermore, Japanese Patent Laid-Open Appln. No. 182263/1984, which was issued after the application of this invention, discloses a method for preparing a surgical cement which comprises mixing α-tricalcium phosphate with an inorganic acid or an organic acid such as nitric acid, hydrochloric acid, phosphoric acid, formic acid, acetic acid, lactic acid and the like.

However, such surgical cements do not satisfy the requirements for compatibility to living tissues and for compressive strength at the same time.

The materials applied to living body are always in contact with the living tissues and are subjected to long-term service. Therefore, they must be safe, that is to say, they must not have harmful effects on the living body such as tumorigenesis and also they do not irritate the tissues around the part where the cement is filled or applied. In addition, they should have a good compatibility to the living cells i.e., a good adhesion to them and a self-ossification, in other words, the assimilation between neonatal bones and the surface of the material.

Under these circumstances, there has been a strong need for the development of materials for living organisms which include components similar to principal components of the teeth or bones and have an excellent compressive strength.

DETAILED DESCRIPTION OF THE INVENTION

The principal object of this invention is to provide surgical cements applicable in the fields of medicine and dentistry, which have components quite similar to those of the teeth or bones of the living organisms, so that they do not cause a foreign substance-formation reaction and they are quite excellent in their compatibility to the living organism.

Another object of this invention is to provide a surgical cement which can be filled into root canals of teeth or defects and vacant parts formed due to diseases or external factors.

A further object of this invention is to provide a surgical cement applicable as a restorative material to repair the alveolar bone disappeared by degeneration and as a filler for tooth and bone fissures which are formed due to external factors such as periodontosis and traffic accidents.

A further object of this invention is to provide a surgical cement of a high compressive strength, which is also applicable to the case where a high strength is required immediately after filling.

A further object of this invention is to provide a surgical cement, thereby the structure and functions of the injured parts and vacant parts (cavity) being repairable or restorable.

Aforementioned objects and other objects of the invention may be accomplished by the following surgical cement.

The surgical cement according to the present invention, comprises self-hardening amorphous tricalcium phosphate, a surgically acceptable water-soluble poly(carboxylic acid) and water.

Furthermore, if desired, there may be added to the cement 0.1 to 10% by weight, preferable 0.1 to 2% by weight of aluminum phosphate in order to improve the compressive strength of the final surgical cement, more or less.

In the self-hardening amorphous tricalcium phosphate used in the surgical cement of this invention, the term "self-hardening" means that the phosphate reacts with surgically acceptable water-soluble poly(carboxylic acid) disclosed below in more detail, to set together.

In order to attain the objects of this invention, powder of the self-hardening amorphous tricalcium phosphate ($Ca_3(PO_4)_2 \cdot XH_2O$) must be used.

Amorphous tricalcium phosphate may generally be obtained by the process which comprises reacting an aqueous solution of calcium salt and an aqueous solution of phosphate, separating the product by filtration under a low temperature condition and drying it.

There may be mentioned, for example, calcium nitrate as the preferred example of the calcium salt and ammonium phosphate is preferably used as the phosphate. The said reaction is preferably carried out at a pH of from 10 to 12 and the reaction is similar to the wet synthesis of the known calcium hydroxide apatite. After the completion of the reaction, the processes such as the separation by filtration, drying and pulverization are carried out at a low temperature. This is an important condition for maintaining the calcium phosphate thus formed in the amorphous state without causing any crystallization.

In said method, it is, therefore, preferable to carry out the separation by filtration, drying and pulverization operation at a temperature of from $-10°$ C. to $+10°$ C. In particular, the upper limit is critical in the process i.e., this is required to maintain the reaction product in the amorphous state as mentioned above.

As the drying operation, there may be mentioned, for example, lyophilization (freeze-drying).

In addition, another essential component other than amorphous tricalcium phosphate is surgically acceptable water-soluble poly(carboxylic acid). All the known poly(carboxylic acid) conventionally used in the surgical cement such as cements containing zinc oxide as principal component or ionomer cements disclosed in U.S. Pat. No. 4,089,830 may be used in the present invention without any difficulties.

The preferred poly(carboxylic acid) are those prepared by the homo-polymerization and co-polymerization of unsaturated aliphatic carboxylic acids and co-polymerization of these acids with other unsaturated aliphatic monomers.

The poly(carboxylic acid) solution which is used in the preferred surgical cement according to the invention may be prepared by any of the customarily used polymerization techniques. For example, polymerization may be carried out in aqueous solution in the presence of ammonium persulphate and various chain transfer agents to give solutions containing up to about 30% of the polymer. This solution may then be concentrated, if necessary, to give a more viscous solution, or freeze-dried to give a solid particulate poly(carboxylic acid).

Various other acrylic monomers may be included in the polymerizing system to give carboxylic acid copolymers having modified properties, provided that the carboxylic acid copolymer is sufficiently soluble in water and reacts with amorphous tricalcium phosphate powder in the required manner.

Particularly preferred poly(carboxylic acids) are (i) homopolymers of acrylic acid, or (ii) copolymers of (a) acrylic acid, preferably in an amount of 60 to 99.9% by weight, as the principal component and (b) a small amount, preferably 0.1 to 40% by weight of at least one unsaturated monomer selected from the group consisting of itaconic acid, maleic acid, fumaric acid, methacrylic acid, aconitic acid, citraconic acid, glutaconic acid, mesaconic acid, tiglic acid and a lower alkylester thereof (the alkyl group having 1 to 5 carbon atoms), and a lower alkylester of acrylic acid ($C_1$ to $C_5$ alkyl).

The surgically acceptable water-soluble poly(carboxylic acid) useful in the surgical cement of the invention desirably has a viscosity-average molecular weight of from 2,000 to 200,000, preferably from 5,000 to 150,000, when determined by the method of Sakamoto (Chem. Abstr., 58, 13160C), 1963.

The poly(carboxylic acid) may be used in the form of powder or in the form of an aqueous solution having a concentration ranging from 10 to 60% by weight, preferably 25 to 55% by weight.

The preferred surgical cement according to the invention comprises (a) 23 to 75% by weight, most preferably 33 to 72% by weight of self-hardening amorphous tricalcium phosphate, (b) 2 to 46% by weight, most preferably 7 to 37% by weight of a poly(carboxylic acid) (component (B)) and (c) 10 to 69% by weight, most preferably 12 to 50% by weight of water.

When the component (B) is used in the form of an aqueous solution having a concentration of 10 to 60% by weight, preferably 25 to 55% by weight, the ratio of the amorphous tricalcium phosphate to the aqueous solution of the component (B) is from 0.3:1 to 3.0:1, preferably from 0.5:1 to 2.5:1.

Even if the aqueous poly(carboxylic acid) solution is used, the respective components must be adjusted so that the amount thereof falls within the aforementioned range.

Furthermore, in the surgical cement of the invention, many other organic acids other than poly(carboxylic acid) may be included preferably in an amount up to 10% by weight, in order to control the setting speed during its application for repairing or restoring the tooth canals and so on.

In the case where the organic acid is used in the form of aqueous solution, the amount of water present in the aqueous solution of the organic acid is previously adjusted so that the total amount thereof falls within the range mentioned above.

As the organic acid which is preferably used in the surgical cement of the invention, there may be mentioned, for example, glycolic acid, glutamic acid, pantothenic acid, lactic acid, tartaric acid, citric acid, malic acid, which may be used singly or as a mixture containing two or more of them.

The surgical cement of the invention can be prepared according to the process which comprises (i) the steps of mixing (a) powder of self-hardening amorphous tricalcium phosphate and (b) component (B) of surgically acceptable water-soluble poly(carboxylic acid) powder, kneading the mixture under the presence of desired amount of water to form fluidized or plastic product or (ii) adding desired amount of aqueous solution of the component (B) to amorphous tricalcium phosphate, kneading the mixture obtained to convert it into fluidized state or plastic state.

Thus, according to the invention, surgical cements can be obtained by combining amorphous tricalcium phosphate with poly(carboxylic acid), the cement being suitable for use as the root canal-filling material, the lining cement, the restorative agent for use in alveolar bones and having a good compatibility to living tissues.

The invention is now explained in more concretely in the light of the following non-limitative examples. In the examples, the terms "parts" and "%" are expressed as "parts by weight" and "% by weight" respectively.

REFERENCE EXAMPLE:

Synthesis of amorphous tricalcium phosphate

The reaction of 3 l of 0.5 mol/l aqueous solution of calcium nitrate $[Ca(NO_3)_2]$ with 2 l of 0.5 mol/l aqueous solution of ammonium hydrogen phosphate $[(NH_4)_2HPO_4]$ was carried out by mixing them under nitrogen gas stream at a temperature equal to or less than 5° C., while adjusting pH to 11 by the addition of aqueous ammonia to the solution.

The resulting precipitates were filtered off below 0° C. and washed with aqueous ammonia and then lyophilized for 24 hours. The product thus obtained was pulverized to form powder having the particle size of less than 300 mesh. The X-ray diffraction pattern thereof simply shows halo and no peak attributed to crystal is observed. This is, hereunder, referred to as "A-TCP".

EXAMPLE

Powder of A-TCP synthesized in the reference example was kneaded with various aqueous poly(carboxylic acid) solutions and, after 24 hours, the products were subjected to compressive strength measurement according to the method of JIS T-6602. The results obtained are shown in Table I.

TABLE I

| Aq. poly(carboxylic acid) Soln. | | | | compressive (strength |
|---|---|---|---|---|
| Composition | Mw* | Concn. (%) | P/L** | (kg/cm²) |
| Polyacrylic acid | 5,000 | 40 | 1.0 | 110 |
| Polyacrylic acid | 30,000 | 40 | 1.0 | 310 |
| Acrylic acid/5% itaconic acid copolymer | 66,000 | 45 | 1.3 | 550 |
| Acrylic acid/15% itaconic acid copolymer | 80,000 | 45 | 1.3 | 600 |
| Acrylic acid/30% itaconic acid copolymer | 30,000 | 45 | 1.3 | 600 |
| Acrylic acid/5% maleic acid copolymer | 15,000 | 45 | 1.3 | 570 |
| Acrylic acid/10% fumaric acid copolymer | 10,000 | 45 | 1.3 | 580 |

*viscosity-average molecular weight.
**the weight ratio of the powder to the solution.

As evident from the results listed in Table I, A-TCP shows a sufficient compressive strength to use as the root canal-filling agent and surgical cement.

COMPARATIVE EXAMPLE

First of all, β-tricalcium phosphate (hereunder referred to as β-TCP) was prepared by calcining the mixture of β-calcium pyrophosphate and calcium carbonate by a conventional method, and hydroxyapatite (hereunder referred to as HAP) was also prepared by reacting calcium hydroxide with an aqueous phosphoric acid solution according to a conventional method. These were kneaded with aqueous poly(carboxylic acid) solution (45% aqueous solution of acrylic acid/itaconic acid copolymer containing 15% itaconic acid moiety: Mw=80,000) and the compressive strength was measured on the resulting products as in the Example. The results thus obtained are shown in Table II.

TABLE II

| Powder | P/L | Compressive Strength (Kg/cm²) |
|---|---|---|
| β-TCP | 1.3 | no hardening |
| HAP | 1.3 | 30 |

As seen from the results listed in Table II, β-TCP has no self-hardening property and HAP has a quite low compressive strength. Although the latter can be set, it cannot be put into practical use, because of its low strength.

What is claimed is:

1. A surgical cement consisting essentially of:
   (a) a component (A) composed of self-hardening amorphous tricalcium phosphate powder;
   (b) a component (B) composed of a surgically acceptable water-soluble poly(carboxylic acid); and
   (c) water.

2. A surgical cement according to claim 1 which consists essentially of:
   (a) from 23 to 75% by weight of amorphous tricalcium phosphate;
   (b) from 2 to 46% by weight of the component (B); and
   (c) from 10 to 69% by weight of water.

3. A surgical cement according to claim 1, in which the component (B) is in the form of an aqueous solution containing from 10 to 60% by weight of the component (B).

4. A surgical cement according to claim 1, which consists essentially of:
   (a) amorphous tricalcium phosphate powder;
   (b) an aqueous solution containing from 10 to 60% by weight of the component (B), and the weight ratio of (a) to (b) being in the range of from 0.3:1 to 3.0:1.

5. A surgical cement according to claim 1, in which the poly(carboxylic acid) is a homopolymer of acrylic acid or a copolymer of (a) acrylic acid as principal monomer with (b) at least one unsaturated monomer selected from the group consisting of itaconic acid, maleic acid, fumaric acid, methacrylic acid, aconitic acid, citraconic acid, glutaconic acid, mesaconic acid, tiglic acid, and lower alkylesters thereof and lower alkylesters of acrylic acid.

6. A surgical cement according to claim 1, in which the poly(carboxylic acid) is the homopolymer of acrylic acid or a copolymer of (a) from 60 to 99.9% by weight of acrylic acid with (b) from 0.1 to 40% by weight of at least one unsaturated monomer selected from the group consisting of itaconic acid, maleic acid, fumaric acid, methacrylic acid, aconitic acid, citraconic acid, glutaconic acid, mesaconic acid, tiglic acid and lower alkylesters thereof and lower alkylesters of acrylic acid.

7. A surgical cement according to claim 1, in which the viscosity-average molecular weight of the poly(carboxylic acid) is in the range of from 2,000 to 200,000, as determined by the method of Sakamoto, Chemical Abstracts, 58, 13160C, 1963.

8. A surgical cement according to claim 1, which further contains at least one other organic acid in an amount up to 10% by weight.

9. A surgical cement according to claim 8, in which said other organic acid is at least one member selected from the group consisting of glycolic acid, lactic acid, glutamic acid, pantothenic acid, tartaric acid, citric acid, malic acid.

10. A process for preparing a surgical cement which consists of the steps of preparing a mixture by admixing (a) self-hardening amorphous tricalcium phosphate powder and (b) a component (B) composed of a powdered surgically acceptable water-soluble poly(carboxylic acid) and adding a desired amount of water, or by adding aqueous solution of the component (B) to amorphous tricalcium phosphate; then kneading the mixture thus obtained to convert the mixture to a fluidized state or a plastic state.

11. A process according to claim 10, in which the amount of amorphous tricalcium phosphate is in the range of from 23 to 75% by weight, that of the component (B) is in the range of from 2 to 46% by weight and the water is used in an amount ranging from 10 to 69% by weight.

12. A process according to claim 10, in which the weight ratio of amorphous tricalcium phosphate to the aqueous solution of the component (B) is in the range of from 0.3:1 to 3.0:1.

* * * * *